(12) United States Patent
Del Vecchio

(10) Patent No.: US 8,852,276 B2
(45) Date of Patent: Oct. 7, 2014

(54) COSMETIC SURGERY SIZER

(75) Inventor: Daniel A. Del Vecchio, Wrentham, MA (US)

(73) Assignee: Lipovera, LLC, North Attleboro, MA (US)

( * ) Notice: Subject to any disclaimer, the term of this patent is extended or adjusted under 35 U.S.C. 154(b) by 0 days.

(21) Appl. No.: 13/542,520

(22) Filed: Jul. 5, 2012

(65) Prior Publication Data

US 2013/0013063 A1  Jan. 10, 2013

Related U.S. Application Data

(60) Provisional application No. 61/504,414, filed on Jul. 5, 2011.

(51) Int. Cl.
*A61F 2/12* (2006.01)

(52) U.S. Cl.
CPC ........... *A61F 2/12* (2013.01); *A61F 2250/0003* (2013.01); *A61F 2250/0013* (2013.01)
USPC .................................................. 623/8; 623/7

(58) Field of Classification Search
CPC ........................................................ A61F 2/12
USPC ................................. 623/7, 8, 23.74; 156/145
See application file for complete search history.

(56) References Cited

U.S. PATENT DOCUMENTS

| | | | |
|---|---|---|---|
| 6,544,287 B1 * | 4/2003 | Johnson et al. | 623/7 |
| 2003/0149481 A1 * | 8/2003 | Guest et al. | 623/8 |
| 2004/0249457 A1 * | 12/2004 | Smith et al. | 623/7 |
| 2006/0210602 A1 * | 9/2006 | Sehl et al. | 424/423 |
| 2011/0270391 A1 * | 11/2011 | Chitre et al. | 623/8 |

* cited by examiner

*Primary Examiner* — David Isabella
*Assistant Examiner* — Yashita Sharma
(74) *Attorney, Agent, or Firm* — Strategic Patents, P.C.

(57) ABSTRACT

Disclosed herein is a sizer for use in cosmetic surgery augmentation procedures, along with methods for using same. The sizer includes an inflatable shell that can be pressurized to assume a shape and size to guide an augmentation procedure, and then deflated for insertion to or removal from the surgical side. The sizer also includes a reinforcing mesh to prevent puncture of the inflatable shell during a surgical procedure.

10 Claims, 4 Drawing Sheets

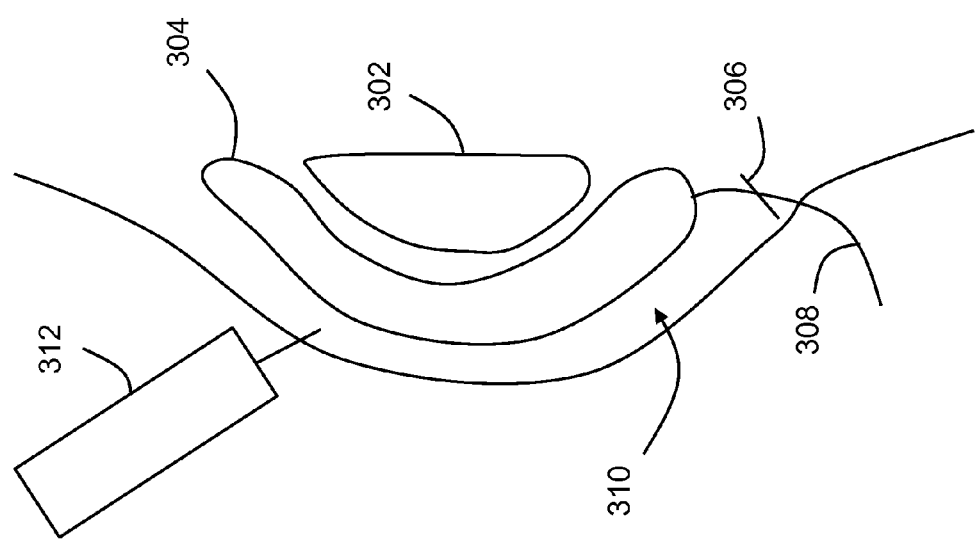

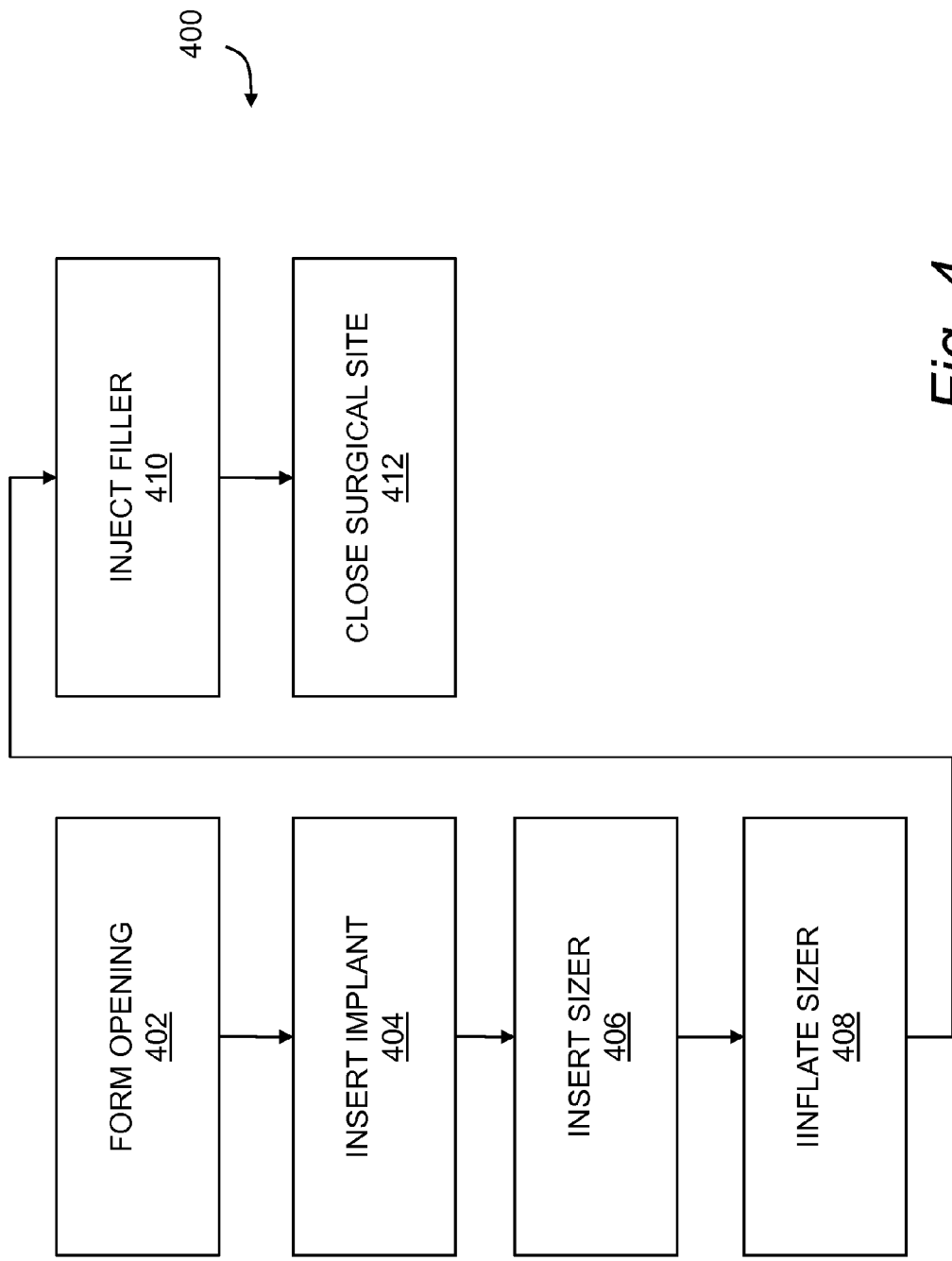

COSMETIC SURGERY SIZER

RELATED APPLICATIONS

This application claims the benefit of U.S. Prov. App. No. 61/504,414 filed on Jul. 5, 2011, the entire content of which is hereby incorporated by reference.

BACKGROUND

A variety of techniques have been devised for breast augmentation. There remains a need for improved methods and systems for use with implants and bulk fillers such as autologous fat.

SUMMARY

Disclosed herein is a sizer for use in cosmetic surgery augmentation procedures, along with methods for using same.

DRAWINGS

Figure 1:
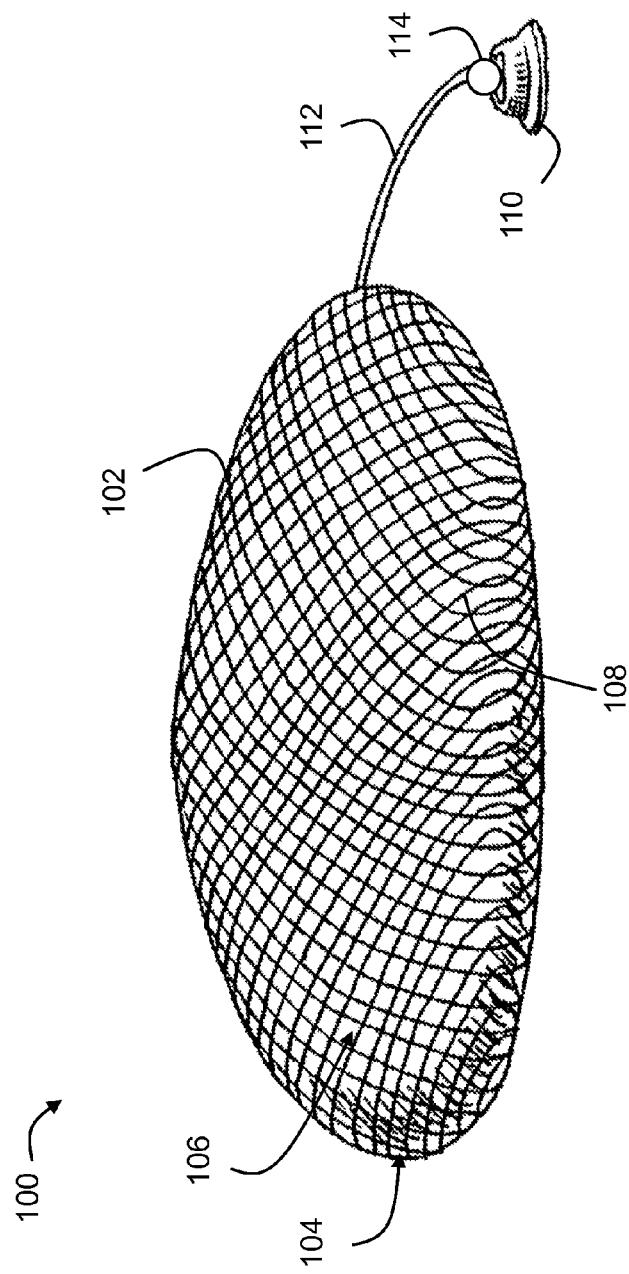
Figure 2:
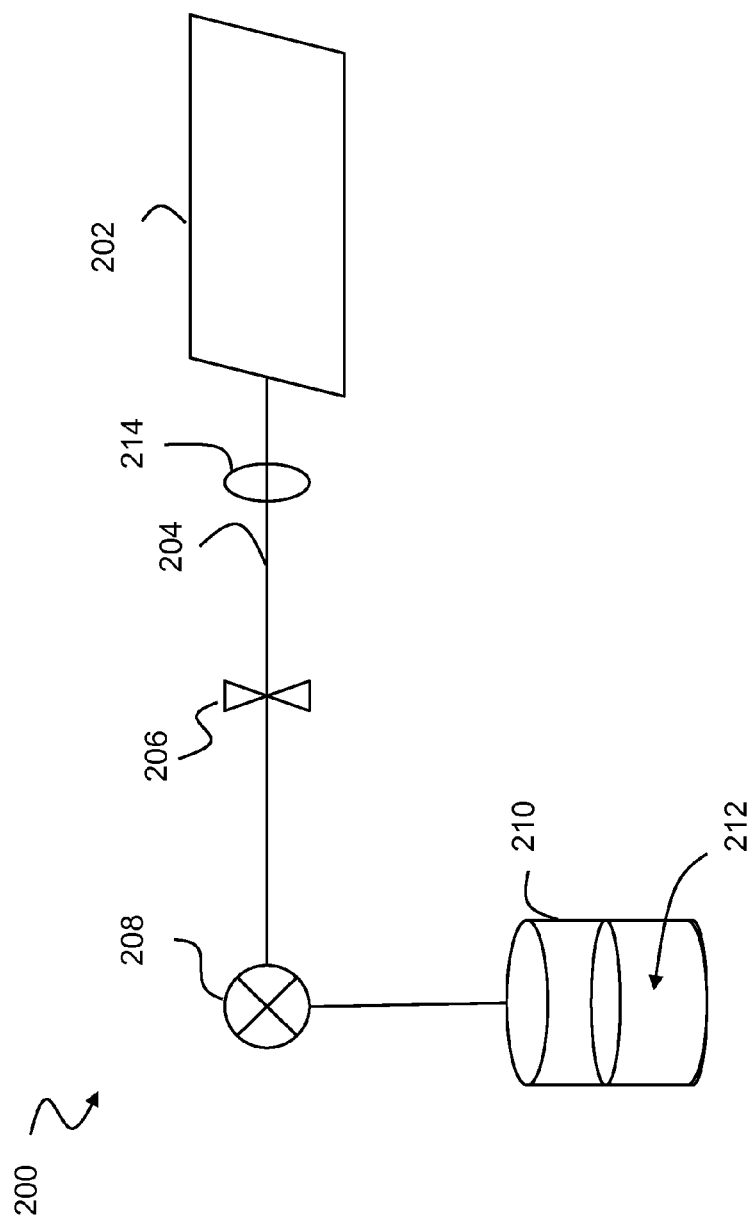

The invention may be more fully understood with reference to the accompanying drawings wherein:

FIG. 1 shows sizer for cosmetic surgery.
FIG. 2 shows a system including a sizer.
FIG. 3 shows a sizer placed for use.
FIG. 4 shows a method for using a sizer.

DETAILED DESCRIPTION

Disclosed herein are sizers for use in cosmetic surgical procedures such as breast augmentation. However it will be understood that the invention disclosed herein is not so limited, and the inventive concepts may be readily adapted to a range of surgical augmentation procedures using, e.g., autologous fat or other biocompatible media used as a bulk filler.

FIG. 1 shows a sizer 100 for cosmetic surgery. In general, the sizer 100 may be formed of an inflatable shell 102 formed of a wall 104 about an interior 106 capable of retaining an inflation medium such as saline solution. In use, the interior 106 may be selectively filled with an inflation medium to inflate and/or deflate the sizer 100. The sizer 100 generally has an inflated form (as depicted in FIG. 1) shaped and sized for use as a sizer during a breast augmentation procedure or the like, that is, supporting the breast, an implant, and surrounding tissue in a desired final shape when positioned within the breast tissue. The sizer 100 also has a deflated form (as shown in FIG. 2) shaped and sized for delivery to a surgical site through an opening. The deflated form may be any generally flattened or otherwise compacted form suitable for rolling, folding, or the like to permit insertion and removal through an opening so that the sizer 100 can be conveniently deployed at a surgical site.

The sizer 100 may be fabricated from a puncture resistant material. The sizer 100 may be fabricated from a medical grade solid silicone and reinforced with a mesh formed of a stainless steel or other flexible metal or material capable of resisting puncture by surgical tools such as a fat grafting needle. The sizer 100 may also or instead be formed of a thickened silicone, or may include a more solid silicone cross-linked shell to protect the sizer 100 from puncture during fat grafting.

In one aspect, the sizer 100 may include a reinforcing mesh 108 within the wall 104. As depicted in FIG. 1 the reinforcing mesh 108 may include an array of interwoven reinforcing fibers arranged into a flexible mesh, which may be formed, e.g., from surgical stainless steel or other biocompatible material. The reinforcing mesh 108 may have a mesh size and strength selected to resist puncture by a surgical instrument such as a needle used to inject a bulk filler during an augmentation procedure. It will be understood that while a mesh of reinforcing fibers is one convenient form of reinforcement, other techniques may also or instead be used. For example, as noted above, the wall 104 may be reinforced with harder or more puncture resistant forms of silicone or other biocompatible material, or any other similar material(s) that can be incorporated into or layered on top of the wall 104 without compromising the ability of the sizer 100 to move between the inflated form and the deflated form The sizer may include a port 110 coupled in fluid communication to the interior 106 of the inflatable shell 102 by a hose 112 or the like. In this manner, an inflatable medium can be added to or removed from the interior 106 through the port 110 in order to inflate the sizer 100 to the inflated form and/or deflate the sizer 100 to the deflated form.

The sizer 100 may be collapsible into a deflated form so that it can be inserted (empty) through a small incision. The sizer 100 may then be inflated (e.g., with saline solution or the like) through the port 110 to an inflated form having a final, desired shape for an augmentation. It will be understood that the desired shape of the sizer 100 may account for surrounding tissue and the like that will also contribute to a final shape for the augmentation after the sizer 100 is removed. The sizer 100 may similarly be evacuated or otherwise deflated to the deflated form for retrieval through the incision. The port 110 may include a valve 114 or similar mechanism to selectively couple the interior of the sizer 100 to a supply of a medium such as saline solution. The valve 114 may be opened during inflation or deflation, and may be closed at other times, such as to maintain a vacuum-deflated sizer 100 in a relatively small shape for packaging, or to maintain a desired pressure to retain the inflated form of the sizer 100 during the course of an augmentation procedure.

In general, the sizer 100 may be used temporarily in a breast surgery or the like as a temporary sizer when fat is to be used over a permanent implant. Thus there is also disclosed herein a method that includes inserting a permanent implant formed of silicone or saline enclosed in a biocompatible carrier in a suitable location, inserting the sizer 100 to provide a desired shape to the implant(s) and surrounding tissue, and injecting fat or other suitable medium(s) into the surrounding tissue to bulk the surrounding tissue into the desired shape. The use of an inflatable sizer as contemplated herein may advantageously permit removal of the sizer after surgery, thereby permitting a permanent breast implant to be placed beneath transplanted fat.

FIG. 2 shows a system including a sizer. In general, the system 200 may include a sizer 202 a hose 204, a valve 206, a pump 208, and a supply 210 of an inflation medium 212.

As depicted, the sizer 202 is flattened into a deflated form in which the sizer 202 can be rolled, folded, or otherwise compacts for deployment to a surgical site through an incision of the like.

The hose 204 may be any hose, tube, or other component(s) and combinations of the foregoing, that might be used to transfer a fluid such as the inflation medium 212 between the supply 210 and the sizer 202 in order to inflate and deflate the sizer 202 as appropriate during a surgical procedure.

The valve 204 may be any device suitable for preventing flow through the hose 204 to and from the sizer 202 so that the sizer 202 can be secured in a particular state of inflation, e.g., in the inflated or deflated form as appropriate during the procedure.

The pump 208 may be any electromechanical pump or pump system suitable to controllably deliver the inflation medium under pressure to the inflatable shell of the sizer 202. In one aspect, the supply 210 may include a syringe body and the pump 208 may be a plunger for the syringe, thus providing a manual delivery mechanism for delivery of the inflation medium 210 to the sizer 202. In another aspect, the pump 208 may include a peristaltic pump or the like for automated inflation of the sizer 202 in order to permit convenient, push-button inflation during a procedure.

A port 214 may provide a mechanical coupling and decoupling point for the system so that the sizer 202 can be attached to the remaining components when ready for use. In general, the supply 210 of the inflation medium 212 may be coupled in fluid communication to the port 214 and the sizer 202 to permit inflation of the sizer 202 from the supply 210.

FIG. 3 shows a sizer placed for use. In general, an implant 302 and a sizer 304 may be inserted through an opening 306 into a desired location. When inflated through a hose 308 into the inflated form, the sizer 304 can provide rigid support that retains surrounding tissue 310 and the implant 302 in a desired shape. In this arrangement, a needle 312 or other suitable instrument may be used to inject a bulk filler into the surrounding tissue 310, while the reinforcing mesh of the sizer 304 protects the sizer 304 against puncture or other damage by the needle 312.

The opening 306 may be an incision in the surrounding tissue 310 at any suitable location, or the opening 306 may be an access port such as a bore of a surgical instrument positioned within such an incision in order to support the incision in an open, operable position and to protect the surrounding tissue 310 from further damage during positioning and use of the sizer 304.

FIG. 4 shows a method for using a sizer. In general, a sizer, which may be a breast implant or any of the other sizers described above, may be placed, e.g., above or below muscle, and may be positioned in a new pocket surgically formed for an augmentation procedure, or a pre-existing pocket such as in the case of a breast implant revision. Fat or similar media may then be transplanted by injection into the overlying breast tissue, thus improving soft tissue coverage and improving the natural look of the resulting augmentation.

As shown in step 402, the method 400 may begin with forming an opening at or near where an augmentation procedure is to be performed. This may include an incision with any suitable surgical instrument. In this step, a surgical pocket may also be formed within tissue at the site for the augmentation procedure and coupled to the opening (i.e., accessible from the opening) to receive a breast implant and a sizer as described below. Where the procedure is a revision to a prior augmentation procedure, an existing tissue pocket may also or instead be used to receive a new implant along with the sizer, e.g., after removal of a previous implant.

As shown in step 404, the method 400 may include inserting a breast implant through the opening into a desired location for augmentation of a breast. The details of breast implants and other augmentation implants are well known in the cosmetic surgery art, and the details are not recounted here. The breast implant may, for example, include a biocompatible carrier containing silicone, saline, or any other suitable filler, or be of any other conventional construction.

As shown in step 406, the method 400 may include inserting a sizer into the opening. The sizer may have a deflated form suitable for inserting through the opening. This may, for example, included deflation into a flat sheet that can be rolled or folded into a compact form. The sizer will in general also have an inflated form to impart a desired shape to the breast after completion of the implant procedure. The sizer may also include a reinforcing layer such as a stainless steel mesh to prevent rupture of the sizer by an instrument used to inject bulk filler at the augmentation site. Inserting the sizer may include inserting the sizer through a bore of a surgical instrument placed into the opening such as a laparoscope or other cosmetic surgical tool that retains and protects the opening during insertion and removal of other tools and the like.

As shown in step 408, the method 400 may include inflating the sizer as generally described above into the inflated form so that the implant and surrounding tissue is supported in a desired shape by the sizer. In this manner, bulk filler can be injected around the sizer, implant, and other tissue while the rigidly inflated sizer urges the bulk filler into a volume of the final, desired shape after augmentation.

Accordingly, as shown in step 410, a bulk filler may be injected into tissue surrounding the breast implant and surrounding tissue while the sizer maintains the desired final shape. The bulk filler may include fat such as autologous fat, or any other suitable bulk filler for surgical augmentation procedures. The bulk filler may be injected using any suitable surgical needles or the like.

As shown in step 412, the surgical site may be closed. This may include related steps such as deflating the sizer, removing the sizer through the opening, and then surgically closing the opening with stitches or any other suitable technique.

It will be appreciated that the methods and systems described above are set forth by way of example and not of limitation. Numerous variations, additions, omissions, and other modifications will be apparent to one of ordinary skill in the art. While particular embodiments of the present invention have been shown and described, it will be apparent to those skilled in the art that various changes and modifications in form and details may be made therein without departing from the spirit and scope of the invention as defined by the following claims, which should be interpreted in the broadest sense allowable by law.

What is claimed is:

1. A device comprising:
   an inflatable shell having a wall and an interior capable of retaining an inflation medium, the inflatable shell having an inflated form shaped and sized for use as a sizer during a breast augmentation procedure and a deflated form shaped and sized for delivery to a surgical site through an opening;
   a reinforcing mesh embedded within the wall of substantially the entire inflatable shell, the reinforcing mesh having a mesh size and a strength selected to protect the inflatable shell against puncture by a surgical needle by a surgical instrument; and
   a port coupled to the interior of the inflatable shell by a hose, whereby the inflation medium is capable of being added to and removed from the interior.

2. The device of claim 1 wherein the opening is an incision in tissue.

3. The device of claim 1 wherein the opening is an access port of a surgical instrument.

4. The device of claim 1 further comprising a supply of the inflation medium coupled to the port.

5. The device of claim 4 further comprising a pump to controllably deliver the inflation medium to the inflatable shell.

6. The device of claim 5 wherein the pump includes a manual delivery mechanism.

7. The device of claim 1 wherein the port includes a valve for selectively coupling to a supply of the inflation medium.

8. The device of claim 1 wherein the inflation medium is saline solution.

9. The device of claim 1 wherein the wall is formed of silicone.

10. The device of claim 1 wherein the reinforcing mesh is a flexible stainless steel mesh.

* * * * *